United States Patent [19]
Elad et al.

[11] Patent Number: 5,266,316
[45] Date of Patent: Nov. 30, 1993

[54] **ISOLATE OF *TRICHODERMA HARZIANUM* I-952 FUNGICIDAL COMPOSITIONS CONTAINING SAID ISOLATE AND USE AGAINST *B. CINEREA* AND *S. SCLEROTIORUM***

[75] Inventors: Yigal Elad, Givat Shmuel; Gilly Zimand, Kfar Ruth; Ilan Chet, Shikun Ezrahi, all of Israel

[73] Assignees: Peri Development Applications (1985) Ltd., Bet Dagan; Yissum Research Development Company of the Hebrew University of Jerusalem, Jerusalem, both of Israel

[21] Appl. No.: 37,541

[22] Filed: Mar. 26, 1993

Related U.S. Application Data

[62] Division of Ser. No. 728,912, Jul. 10, 1991, Pat. No. 5,238,690.

[30] Foreign Application Priority Data

Jul. 12, 1990 [IL] Israel .......................................... 95066

[51] Int. Cl.⁵ .......................... A01N 63/00; C12N 1/20
[52] U.S. Cl. ................................ 424/93 Q; 435/252.1
[58] Field of Search .................... 435/252.1; 424/93 Q

[56] References Cited

U.S. PATENT DOCUMENTS

| | | | |
|---|---|---|---|
| 4,489,161 | 12/1984 | Papavizas | 435/254 |
| 4,574,083 | 3/1986 | Baker et al. | 424/93 Q |
| 4,678,669 | 7/1987 | Ricard | 424/93 Q |
| 4,713,342 | 12/1987 | Chet et al. | 435/254 |
| 4,797,361 | 1/1989 | Montenecourt | 435/198 |
| 4,837,155 | 6/1989 | Tabachnik | 435/254 |
| 4,915,944 | 4/1990 | Chet et al. | 424/93 Q |
| 4,950,472 | 8/1990 | Janisiewicz | 424/93 Q |
| 5,034,389 | 7/1991 | Gyure et al. | 514/251 |

*Primary Examiner*—Douglas W. Robinson
*Assistant Examiner*—Deborah K. Ware
*Attorney, Agent, or Firm*—Browdy and Neimark

[57] ABSTRACT

The present invention relates to a novel biologically pure culture of *Trichoderma Harzianum*, I-952, to biological control compositions containing same and to methods of protecting flowering plants and fruits from the disease gray mold, caused by *B. Cinerea* and the disease white rot caused by *S. Sclerotiorum* with the compositions.

10 Claims, No Drawings

ISOLATE OF *TRICHODERMA HARZIANUM* I-952 FUNGICIDAL COMPOSITIONS CONTAINING SAID ISOLATE AND USE AGAINST *B. CINEREA* AND *S. SCLEROTIORUM*

CROSS-REFERENCE TO RELATED APPLICATIONS

The present application is a division of U.S. Ser. No. 07/728,912, filed Jul. 10, 1991, now U.S. Pat. No. 5,238,690.

BACKGROUND OF THE INVENTION

The present invention relates to antifungal compositions, particularly to biological control compositions containing *Trichoderma harzianum* and to methods of protecting plants from pathogenic fungi *Botrytis cinerea* and *Sclerotinia sclerotiorum* with such compositions.

Gray mold, incited by *Botrytis cinerea* Pers: dr. and white rot incited by *Sclerotinia sclerotiorum* Lib: de Bary are serious problems in many crops around the world. The pathogen attacks many crops including grapes, vegetables and ornamentals. Crops are attacked when grown in the open or in structures under cover. If not adequately controlled, gray mold and white rot can cause substantial pre-harvest as well as post-harvest losses at storage and transport. The pathogens attack all parts of the plants including flowers, fruits, leaves, stems, branches, phyloclades, bulbs or seeds.

Chemical fungicides are widely used to control the disease. However, *B.cinerea* has developed resistance to common fungicides used. Among these are dicarboximide fungicides and benzimidazole fungicides. In many places, farmers do not have any solution for the problem because of resistance and in other places or crops this is likely to happen in the future.

Gray mold and white rot epidemics are usually severe when high humidity, temperatures between 10° C.-25° C. and wetness over the sensitive organs of the plant prevail.

The use of antagonistic micro-organisms in controlling plant pathogenic fungi has been the subject of extensive research. One of the most frequently studied antagonists in relation to biological control is the genus Trichoderma (Y. Elad et al., 1982, Can. J. Microbiol. 28: 719-725; I. Chet and R. Baker, 1981, Phytopathology 71: 286-290; M. N. Schroth and J. G. Hancock, 1981, Ann. Rev. Microbiology 35: 459-463; Y. Elad et al., 1981, Plant Disease 65: 675-677; Y. Elad et al., 1980, Phytopathology 70: 119-121; I. Chet et al., 1979, in B. Scrippers and W. Gams. eds., Soil Borne Plant Pathogens", Academic Press, New York, N.Y.; Y. Hadar et al., 1979, Phytopathology 69: 64-68; C. Dennis and J. Webster, 1971, Trans. Br. mycol. Soc. 57 (3), 363-369: Y. Elad., (1990) Phytoparasitica, 18:99-105).

Species or strains of Trichoderma may be differentially antagonistic to different species of fungi (H. D. Wells et al., 1972, Phytopathology 62: 442-447). Such differences in antagonism have been found both within and between species of Trichoderma (D. K. Bell et al., 1982, Phytopathology 72: 379-382). Therefore each isolate of Trichoderma, regardless of its species, has different features in abilities to contract plant diseases.

*B.cinerea* and *S.sclerotiorum* are sensitive to antagonism by competition of other microorganisms. Germination of spores and growth of hyphae of this plant pathogen and infection of host plants can be reduced when nutrients and space are limited. Such a mechanism can be a basis for successful biological control of gray mold and white rot. More-over, the antagonist should be able to survive in the same niche for a long time and be active against the pathogen at the same time.

SUMMARY OF THE INVENTION

In accordance with the present invention, there is provided a novel antagonist strain of the species *T. harzianum* has been discovered, which is active against the plant pathogens *Botrytis cinerea* and *Sclerotinia sclerotiorum*. The antagonist is useful in controlling the plant disease gray mold which is caused by *B.cinerea* and white rot caused by *S.sclerotiorum*. The strain of *T. harzianum* T-39 (I-952) has been cultured in a biologically pure culture.

*T. harzianum* T-39 (I-952) can be applied on the canopy of plants alone in the tank mix, and in alternation with the different fungicides used for controlling gray mold. The novel strain of *T. harzianum* can be grown, maintained and be mixed with a suitable agriculturally acceptable carrier to produce a fungicidally active biocontrol composition useful in controlling diseases caused by *B.cinerea*, and *S.scleotiorum*. The biocontrol composition may also contain a food base for the mycoparasite or the carrier itself may also serve as a food base.

In one of the embodiments of the invention, the biocontrol composition may also contain a suitable agriculturally acceptable adhesive. The biocontrol agent *T. harzianum* T-39 (I-952) reduces disease caused by *B. cinerea* and *S. sclerotiorum* by 50%-90% as compared with non-treated controls. The antagonist is capable of maintaining high population over leaves and fruits of the treated plants in greenhouses, vineyards or elsewhere. *T. harzianum* T-39 (I-952) is capable of competing with the fungus *B. cinerea* and *S.sclerotiorum* for nutrients and space. This gives this isolate its unique ability to control the disease.

The invention also concerns methods of using this biocontrol composition as a fungicide against gray mold. Effective amounts of the biocontrol composition are applied to various parts of the plant.

In a specific embodiment of the invention, a chemical fungicide is included in the biocontrol composition. *T. harzianum* T-39 (I-952) possesses resistance to chemical fungicides which would kill or retard the growth of other fungi. Resistance to such chemical antagonists enables the invention to be used in integrated chemical and biological control of *B. cinerea* and *S.sclerotiorum*. Alternatively, the chemical fungicide is applied alone either prior to or after treating with *T. harzianum* T-39 (I-952).

DETAILED DESCRIPTION OF THE INVENTION

A novel antagonistic strain of the species *Trichoderma harzianum* has been discovered which is active against the plant pathogenic fungus *Botrytis cinerea*. The preferred strain of this novel antagonist was isolated from the natural microflora of the phyloplane of cucumber fruit. The antagonistic fungus was cultured in biologically pure form, tagged as T-39 and identified according to the creteria of Rifai (Rifai, M., Mycol. Pap. 116). This preferred strain of *Trichoderma harzianum* Rifai T-39 is deposited with Institute Pasteur, Collection Nationale de Cultures de Microorganisms, Paris, France, pursuant to the provisions of the Budapest Treaty on the International Recognition of the Deposit of Microorganisms for the Purpose of Patent procedure under accession number I-952.

*T. harzianum* Rifai T-39 (I-952) and the mutants derived therefrom may be used to control gray mold caused by *B. cinerea* and white rot caused by *S. sclerotiorum*. In addition to antagonistic ability, *T. harzianum* T-39 (I-952) has long term survivability on the canopy of plants. It can be applied on plants in alteration with fungicides which are aimed against gray mold-examples are benomyl, carbendazim, vinclozolin, iprodione, procymidon, dichlofluanide, tebuconazole, prochloraz, fenethanil, diethefencarb, metomeclan, chlorothalonil, and mixtures of these fungicides.

*T. harzianum* T-39 (I-952) possesses resistance to the following pesticides with which it may be applied on plants in various agrosystems: polyoxin D, polyoxin B, TMTD, $CuSO_4.5H_2O$ diphenylamine, folpet, tridemorph, bitertanol, dimethirimol, triforine, dichloronit, roaniline, bupirimate, hexaconazole, miclobutanil, fenitrothion, phosethyl-Al, propiconazole, azinphosmethyl, chlorpyrifos, mancozeb, endosulfan, methomyl, tridimefon, quinomethionate, diniconazole, methidathian copper oxychloride, imazalil, oxadixyl, cymoxanil, metalaxil, triadimenol, ditalimfos, sulphur, and penoconazole.

In addition to its wide range of antagonism and resistance to chemical fungicides and pesticides, *T. harzianum* T-39 (I-952) is capable of long term survivability and of controlling gray mold and white rot throughout a 3° C. to 30° C. temperature range. This additional characteristic makes the present invention a versatile biocontrol agent suitable for application in semi-arid as well as temperate agricultural zones, in greenhouses or in the open, in storage or transportation of agricultural products.

Methods of application of *T. harzianum* T-39 (I-952) are by means of conidia, chlamydospores, or hyphal segments, or by means of each combination of them, directly to the canopy of the plants. Direct application of the antagonist, however, seems to be less effective than the application of a bicontrol composition which contains *T. harzianum* T-39 (I-952) and an agriculturally acceptable carrier.

These biocontrol compositions may be in a solid or liquid form and may include other adjuvants such as emulsifiers, suspending agents, sticking agents, etc. The solid compositions may be in the form of dusts, granules, or wettable powders, whereas the liquid compositions may be in the form of aqueous or non-aqueous media, in solutions, suspensions, dispersions, dispensions, or concentrate form.

The quantity of spores, hyphae, or chlamydospores of the antagonist in the composition should be at least 10 cells per gram of composition. Propagation of these spores depends upon growth conditions within the composition or on the plants on which it is applied. Such factors as the storage time of the composition may have an effect on the growth conditions of the antagonist and therefore it is prepared in a composition which contains a suitable food base.

In certain embodiments of the invention, the carrier may constitute wholly or in part a food base for the antagonist. The food base and carrier provide the antagonist with sufficient nutrients and a favorable micro-environment facilitating its establishment and long-term micro-environment and long term survival on plant organs.

In other embodiments of the invention the biocontrol compositions may also contain another pesticide or another biocontrol agent such as another isolate of an antagonistic microorganisms such as Trichoderma or another species of microorganism.

For application on plants the biocontrol composition is applied at the rate of 10–1000 grams in 10–300 ml water for 1000 $m^2$ of crop, or at the rate of 0.05–0.5% w/w of water on pre-and post-harvested agricultural products.

The range of host plants that are subject to attack by *B. cinerea* or *S. sclerotiorum* is very broad. This invention is effective in controlling diseases caused by this plant pathogen over this wide range and is effective in protecting such plants as cucumber, tomato, pepper, grape, rose, strawberry, eggplant, bean, geranium, lettuce, carrots and other plants.

While the invention will now be described in connection with certain preferred embodiments in the following examples, it will be understood that it is not intended to limit the invention to these particular embodiments. On the contrary, it is intended to cover all alternatives, modifications and equivalents as may be included within the scope of the invention as defined by the appended claims. Thus the following examples which include preferred embodiments, will serve to illustrate the practice of this invention, it being understood that the particulars shown are by way of example and for purposes of illustrative discussion of preferred embodiments of the present invention only and are presented in the cause of providing what is believed to be the most useful and readily understood description of procedures as well as of the principles and conceptual aspects of the invention.

EXAMPLE 1

A Strain Trichoderma species was isolated from cucumber fruit as follows:

Fruits were shaken in water at 200 rpm. Portions of the wash water were diluted one time and 0.1 ml was spread on selective medium agar plates (Elad et al., Phytoparasitica, 1981, Vol. 9, pp. 59–67). The resultant pure strain was named T-39. The isolate T-39 was identified according to the key suggested by Rifai (Rifai, M., 1969, Mycol., Pap. 116) as *Trichoderma harzianum*.

EXAMPLE 2

*T. harzianum* T-39 (I-952) was grown on a solid state medium based on starch as a major food source and celite as a water reservoir. The growth starts by inoculating the solid medium with Trichoderma. The mixture of all the food ingedients, the celite, and the inocular are granulated and are then incubated in a room kept at 25° C. During the 10 days of the growth the medium is turned over twice and then dried and ground. The end product contains twice and then dried and ground. The end product contains $5 \times 10^9$ to $1 \times 10^{10}$ colony forming units (CFU) per gram. Viability tests showed that an initial $8.5 \times 10^9$ CFU/g dry weight kept at room temperature for six months changed only slightly to $7.5 \times 10^9$ CFU/g dry weight and after 12 months to $7 \times 10^8$ CFU/g dry weight.

EXAMPLE 3

*T. harzianum* T-39 (I-952) was tested in growth medium (potato dextrose agar) amended with various fungicides and pesticides. Germination of conidia was evaluated 24 hours after inoculation. In addition, the growth of mycelium within 3-4 days after inoculation at 20°±2° C. was also evaluated. Pesticides were arranged in groups according to their ability to inhibit *T. harzianum* T-39 (I-952) (in Tables 1 and 2.

EXAMPLE 4

Conidia of Trichoderma spp. isolates were sprayed on various plants. Inoculation of the treated plants with *B. cinerea* was carried out thereafter. All treatments were incubated in a dew chamber at 16°±2° C. to develop gray mold. Disease incidence was evaluated within 5 to 10 days. The percentage of disease incidence by the various isolates of Trichoderma spp. is presented in Table 3. The results show that *T. harzianum* T-39 (I-952) is far superior to the other isolates.

EXAMPLE 5

The effect of *T. harzianum* T-39 (T-952) against gray mold of grapes was tested by spraying in vineyards alone, as a composition with Iprodione, or alternatively with Iprodione in three different locations according to the recommended program in each region. The percent berries infected is presented in Table 4. The results show improved control of the disease when using *T. harzianum* T-39 (I-952).

EXAMPLE 6

*T. harzianum* T-39 (I-952) was sprayed on rose plants kept in a commercial heated greenhouse kept at 15° C.±3° C. and naturally infested with *B. cinerea* and compared with the effect of a mixture of tebuconazole and dichlofluanide. The active biocontrol agents were sprayed at a volume of 1000 l/ha in water. Plots of 5 m×1 m were randomized scattered in 5 replicates. Table 5 shows that *T. harzianum* T-39 (I-952) effectively controls stem infections of *B. cinerea* when applied alone or alternately with a mixture of tebuconazole and diclofluanide.

EXAMPLE 7

Conidia of *T. harzianum* T-39 (I-952) were sprayed on cut rose flowers naturally infected with *B. cinerea*. Flowers were incubated in a humidity chamber for six days and the severity of the gray mold was then examined. As shown in Table 6, a spray containing $10^7$ conidia per ml is more useful for the biocontrol of rose gray mold.

EXAMPLE 8

Compositions of *T. harzianum* T-39 (I-952) in 1000 l/ha in water were sprayed alone, in conjunction with, or alternatively with chemical fungicides on table grapes in vineyards naturally infested with gray mold caused by *B. cinerea*. The infection was monitored on the bunches in the vineyards, or on harvested bunches during incubation in a mist chamber. The results as shown in Table 7 shows, that *T. harzianum* T-39 (I-952) effectively controls gray mold in table grapes applied in various ways.

EXAMPLE 9

Compositions of *T. harzianum* T-39 (I-962) in a volume of 1000 l/ha were sprayed on tomatoes in a greenhouse. Plots consisted of 20 plants randomized in five replicates. Naturally occurring *B. cinerea* was monitored on stems, leaves and fruit. Symptoms on the fruits were either regular rot or ghost spots. As shown in Table 8, all symptoms of gray mold of tomato plants were controlled by *T. harzianum* T-39 (I-952).

EXAMPLE 10

A composition of *T. harzianum* T-39 (I-952) was sprayed on strawberry fruits naturally infested with *B. cinerea*. Treated and non-treated fruits were incubated in a humidity chamber. Table 9 shows that T-39 successfully reduced gray mold.

EXAMPLE 11

Compositions of *T. harzianum* T-39 (I-952) were sprayed on cucumber plants in unheated greenhouses at various locations. Plots consisted of at least 10 plants, repeated 5-6 times, in a randomized block design. Gray mold occurred on the fruits and stems at different rates according to the conditions in the specific greenhouse and the natural population of *B. cinerea*. *T. harzianum* T-39 (I-952) was sprayed alone, in a tank mixture with another fungicide, or alternatively with another fungicide. Table 10 shows that compositions containing *T. harzianum*(I-952) significantly reduced the incidence of the disease.

EXAMPLES 12-13

The objective of these tests was to determine if there is any effect on the process of preparing wine made from grapes treated with compositions containing *T. harzianum* T-39 (I952). A preparation of *T. harzianum* T-39 (I-952) was sprayed at a rate of 4 kg/ha on the grapes (cv. Sauvinion Blanc) in vineyards located in Ortal (Golan Heights, Northern Israel). Spray was conducted in mid August, 1989, by a back sprayer to two rows of vines, each 20 m long. Non-sprayed rows of vines, separated by 3 rows of buffer rows, served as control. No fungicides were sprayed in the experiment site, but all other treatments were carried out according to the recommendations in the region. On 1.9.1989 ten samples of 10 kg grapes were randomly sampled in the vineyard and transferred to the laboratory. Grape juice was produced out of each sample of grapes. $SO_2$ was added to the juice after production and 6 hours later yeasts and nutrients were added according to recommendations. The fermented juice was incubated in 1 liter bottles with a pipe letting the $CO_2$ out from the system.

The Brix level (%) was measured with a Brix counter and the results are shown in Table 11. The population of yeast cells was counted by a heamocytometer and the results are shown in Table 12.

From these results it can be concluded that total soluble solids as measured by the Brix method did not differ between the control and that stemming from grapes treated with T-39. Furthermore, while the initial measurements showed a drop in the yeast cell population, this was not statistically significant and after 8 days the results were essentially the same. Therefore the use of *T. harzianum* T-39 (I-952) on grapes has no significant effect on the production therefrom of ethanol. Finally, wine tasting revealed no difference in odor, color, taste and clarity between wine made from the control juice and wine whose grapes were treated with *T. harzianum* T-39 (I-952).

EXAMPLE 14

Conidia of *T. harzianum* T-39 (I-952) were sprayed on rose flowers. flowers were then monitored for the level of *T. harzianum* population over them during one week after spray. The level of *T. harzianum* population was determined by washing the flowers in water containing 0.001M Tween-20 serial dilution of the wash water, and plating on Trichoderma selective medium. Colonies were counted after incubation for 5 days at 20° C. The population level of *T. harzianum* did not drop drastically during the week, as shown in Table 13.

EXAMPLE 15

A composition of *T. harzianum* T-39 (I-952) was sprayed at a rate of 0.2% to 0.4% on strawberry plants in field plots (4 replicates of 10×1.6 meters) arranged in randomized blocks and the results compared with the effect of chemical fungicides. After four weeks the disease incidence on the strawberries was reduced by *T. harzianum* T-39 (I-952) a rate similar to that by the fungicides, as shown in Table 14.

EXAMPLE 16

A composition of *T. harzianum* T-39 (I-952) was applied at a rate of 0.2% to 0.4% to carrots naturally infected by *S. sclerotiorum*. The carrots were treated after harvest and incubated in a humidity chamber. After two weeks the disease severity of white rot was tested. It can be seen that the white rot of carrots was reduced significantly by both rates of T-39; but was not reduced by thiobendazole applied at the recommended rate, as shown in Table 15.

EXAMPLE 17

A composition of *T. harzianum* T-39 (I-952) was sprayed on cucumber plants in a greenhouse. The population of T-39 was measured on the leaves and fruit as a factor of time. It can be seen from Table 16, that the biocontrol agent established itself on the canopy of the cucumber plants.

TABLE 1

Sensitivity of *T. harzianum* T-39 (I-952) To Pesticides In PDA.

| A. Highly inhibiting agents[a] | Moderately inhibiting agents[b] |
|---|---|
| Vinclozolin | Diethofencarb |
| Iprodione | Polyoxin D |
| Carbendazim | Polyoxin B |
| Benomyl | Dichlofluanid |
| Carbendazim + diethofencarb | Thiram |
| Chlorothalonil | CuSO$_4$.5H$_2$O |
| Metomeclan | Diphenylamine |
| Fenkuconazole | Folpet |
| Procymidon | Tridemorph |
| Fluazinon | Bitertanol |
| Tebuconazole | |
| Prochloraz | |

[a]Inhibition at a pesticide concentration of 2 ppm or less.
[b]Inhibition at a pesticide concentration of 2–15 ppm.

TABLE 2

Sensitivity Of *T. harzianum* T-39 (I-952) To Pesticides In PDA.
No Inhibition[a]

| | |
|---|---|
| Dimethirimol | Methomyl |
| Triforine | Triadimefon |
| Dichloronitroaniline | Quinomethionate |
| Bupirimate | Diniconazole |
| Hexaconazole | Methidathion |
| Miclobutanil | Copper oxychloride |
| Fenitrothion | Imazalil |
| Phosphethyl A1 | Metalazil |
| Propiconazole | Oradizyl + Cymoxanil + Mancozeb |
| Azinphos methyl | Triadimenol |
| Chloropyrifos | Ditalimfos |
| Mancozeb | Sulphur |
| Endosulfan | Penconazole |

[a]Inhibition at a pesticide concentration of greater than 15 ppm.

TABLE 3

Severity Of Gray Mold Disease In The Presence Of Trichoderma spp. Isolates Applied As Conidial Suspensions

| | | Percentage Of Disease Incidence | | | |
|---|---|---|---|---|---|
| Isolate | Origin | Tomato | Pepper | Geranium | Rose |
| Control | — | 100 | 100 | 100 | 100 |
| T-39 | Cucumber[a] | 61 | 46 | 6 | 20 |
| T-44 | Soil | 83 | 80 | 126 | 25 |
| TOM | Soil | 83 | 56 | 111 | 40 |
| T-502 | Soil | 67 | 56 | 111 | 25 |
| T-672 | Soil | 100 | 53 | 36 | 58 |
| T-35 | Soil | 100 | 80 | 44 | 50 |
| T-Y | Soil | 100 | 60 | 36 | 57 |
| T-164G | Cucumber[a] | 100 | 80 | 92 | 40 |
| T-180H | Soil | 100 | 60 | 180 | 50 |
| T-80 | Soil | 100 | 73 | 180 | 65 |
| T-RCTI | Grapes/France | 78 | 80 | 17 | 65 |
| T-28 | Soil | 67 | 66 | 55 | 65 |
| T-65G | Eggplant[a] | 122 | 66 | 64 | 83 |
| T-315 | Soil | 133 | 66 | 100 | 83 |
| T-FOR | Soil | 89 | 80 | 100 | 58 |
| T-94 | Soil | 100 | 56 | 111 | 75 |
| T-501 | Soil | 66 | 93 | 83 | 25 |
| T-132G | Tomato[a] | 100 | 73 | 110 | 40 |
| T-CW 10 | Soil | 89 | 100 | 72 | 83 |
| T-GAM | Soil | 100 | 68 | 127 | 108 |
| T-GEN-12 | Soil | 88 | 80 | 154 | 100 |
| T-33 | Soil | 96 | 86 | 50 | 100 |
| T-177G | Cucumber[a] | 100 | 86 | 62 | 60 |
| T-55 | Soil | 100 | 86 | 100 | 200 |
| T-199G | Grapes | 100 | 100 | 100 | 163 |
| T-59G | Grapes | 100 | 73 | 100 | 125 |
| T-133G | Grapes | 68 | 73 | 130 | 100 |
| T-191G | Tomato | 100 | 75 | 72 | 100 |
| T-192G | Eggplant[a] | 100 | 80 | 50 | 63 |

[a]Greenhouse.

TABLE 4

Effect Of *T. harzianum* T-39 (I-952) And Iprodione Against Gray Mold In Wine Grapes.

| | | | Carignan Variety in | | Gamay in Chazay | Gamay in Villefranch[d] | |
|---|---|---|---|---|---|---|---|
| | | | Carcassonne d'Azergnes | | | | |
| Active Ingredient | Dose[a] | Spray Program[c] | % Berries Infected | | | | |
| | | | 22/3[d] | 10/4[e] | 14/4[f] | 4/4[g] | 21/4[h] |
| Untreated | | | 19.7 | 48.2 | 33.3 | 3.1 | 10.4 |
| Iprodione | 500 | ABCD | | | | 0.5 | 1.8 |
| | 750 | ABCD | 5.0 | 3.3 | 14.5 | 0.6 | 3.3 |
| T-39 | 4[b] | ADCD | 5.0 | 18.4 | 20.0 | 2.8 | 7.0 |
| Iprodione and T-39 | 500 4[b] | ADCD | | | 15.9 | 0.6 | 2.4 |
| T-39 followed | 4 | AB | 2.0 | 11.0 | | | |

TABLE 4-continued

Effect Of *T. harzianum* T-39 (I-952) And Iprodione Against Gray Mold In Wine Grapes.

by Iprodione 750 CD

[a] gram active ingredient per hectare.
[b] 4 kg/ha of formulation.
[c] A = cap fall; B = Bunch Clos; C = Veraison; D = Pre-harvest
[d] 22 days after treatment 3.
[e] 10 days after treatment 4.
[f] 14 days after treatment 4.
[g] 4 days after treatment 4.
[h] 21 days after treatment 4.

| Location | Dates of Treatments |
|---|---|
| Cascassonne | 21.6.1989; 5.7.1989; 17.8.1989; 11.9.1989. |
| Chazay d'Azerguer | 14.6.1989; 4.7.1989; 3.8.1989; 22.8.1989. |
| Villefranche | 15.6.1989; 4.7.1989; 1.8.1989; 21.8.1989. |

TABLE 5

Effect Of *T. harzianum* T-39 (I-952) On The Incidence Of Gray Mold On Stems Of Rose Bushes

| Treatment | Cumulative Number Of Infected Stems Per 10 Plants |
|---|---|
| Non-treated Control | 10.8 |
| T-39 (4 g/l) | 5.6 |
| Terbuconazole + Dichlofluanide | 3.8 |
| T-39 followed by Tebuconazole + Dichlofluanide | 3.8 |
| Polyoxin B (1.0 g/l) | 3.8 |

TABLE 6

Effect of Conidia Of *T. harzianum* T-39 (I-952) Sprayed On Rose Flowers Naturally Infested With *B. Cinerea*[a]

| Concentration of Conidia (per ml) | Disease Index[b] |
|---|---|
| 0 | 2.7 |
| $10^6$ | 2.0 |
| $10^7$ | 1.0 |

[a] After 6 days in a humidity chamber.
[b] Key:
0 = No disease.
5 = completely infected.

TABLE 7

Effect Of *T. harzianum* T-39 (I-952) Sprayed in the Vinegard on Gray Mold of Table Grapes

| | Infections per 10 Vines | | |
|---|---|---|---|
| Treatment | CV. Barlinka[a,b] | CV. Shami[a,b] | Cu. Shami[a,c] |
| Untreated control | 6.2 | 20.3 | 5.6 |
| T-39 (4 g/l) | 2.8 | 13.3 | 2.7 |
| Folpet | 1.8 | — | — |
| Iprodione (0.5 g/l) | — | 8.6 | 2.3 |
| Diethofencarb + Carbendazim (0.25 g/l each) | — | 11.3 | 0.3 |
| T-39 + Iprodione | — | 3.0 | 1.3 |
| T-39 alternated by a mixture of Diethocarb and Carbendazim | — | 11.0 | 3.0 |

[a] Cultivar of grape.
[b] Tested in the vineyard.
[c] Tested 7 days after harvest.

TABLE 8

Effect of *T. harzianum* T-39 (I-952) On Tomato Plants In Greenhouses

| Treatment | Fruit Rot[a] | Infected Leaves[a] | Infected Stems[a] | Fruit Ghost Spots[b] |
|---|---|---|---|---|
| Nontreated control | 39.8 | 20.4 | 1.2 | 2.6 |
| T-39 (4 g/l) | 23.8 | 13.0 | 0.2 | 0.5 |
| Iprodione (0.5 g/l) | 15.0 | 4.6 | 0.2 | 0.3 |

[a] Number of infections per 10 plants.
[b] Disease index:
0 = Healthy fruit.
5 = Fruit completely covered with spots.

TABLE 9

Effect Of *T. harzianum* T-39 (I-952) On The Post-Harvest Control Of Gray Mold In Strawberry

| Days of Incubation in Humidity Chamber | Disease Index[a] | |
|---|---|---|
| | Non-treated Fruit | Treated Fruit |
| 9 | 3.0 | 1.6 |
| 11 | 3.5 | 2.4 |
| 13 | 4.6 | 2.8 |

[a] Disease Index:
0 = Healthy.
5 = Completely destroyed.

TABLE 10

Effect Of *T. harzianum* T-39 (1952) On Infections of Cucumber Fruits And Stems In Various Locations In Israel[a]

| | Disease Incidence As Number of Infections Per 10 Plants | | | | | | | |
|---|---|---|---|---|---|---|---|---|
| | Ara[b] | | Herut[b] | Gadish[b] | | Ibtan[b] | | Ahitu |
| Treatment | Fruit | Stem | Fruit | Fruit | Stem | Fruit | Stem | Stems |
| Nontreated Control | 33.3 | 12.3 | 174.7 | 15.7 | 12.0 | 34.3 | 48.0 | 3.75 |
| Vinclozolin (0.5 g/l) | 18.3 | 4.3 | — | — | — | — | — | — |
| Iprodione (0.5 g/l) | — | — | 88.0 | 5.5 | 4.8 | 13.4 | 16.8 | 1.5 |
| T-39 (2 g/l) | 10.8 | 2.0 | — | — | — | — | — | — |
| T-39 (4 g/l) | — | — | 14.1 | 3.8 | 5.5 | 14.0 | 24.0 | 2.0 |
| T-39 (4 g/l) mixed with Iprodione (0.5 g/l) | — | — | 15.0 | 2.8 | 1.5 | 15.4 | 15.3 | 0.2 |
| T-39 (4 g/l) | — | — | — | — | — | 12.5 | 22.0 | — |

TABLE 10-continued

Effect Of T. harzianum T-39 (1952) On Infections of Cucumber Fruits And Stems In Various Locations In Israel[a]

| Treatment | Disease Incidence As Number of Infections Per 10 Plants | | | | | | | |
|---|---|---|---|---|---|---|---|---|
| | Ara[b] | | Herut[b] | Gadish[b] | | Ibtan[b] | | Ahitu |
| | Fruit | Stem | Fruit | Fruit | Stem | Fruit | Stem | Stems |
| alternated by Iprodione (0.5 g/l) | | | | | | | | |

[a]Sprayed at a volume of 1000 l/ha.
[b]Location in Israel.

TABLE 11

Effect Of T. harzianum T-39 (I-952) On The Brix Level Of Grape Juice Made From Grapes Treated With T-39

| Treatment in Vineyard | Days Of Incubation | | | | |
|---|---|---|---|---|---|
| | 1 | 3 | 8 | 11 | 17 |
| Control | 16.0 | 11.8 | 6.4 | 6.3 | 6.3 |
| Trichoderma T-39 (I-952) | 15.5 | 11.1 | 6.2 | 6.2 | 6.2 |

Differences between treatments at each date were statistically not significant, according to Duncan's Multiple Range Test (P = 0.05).

TABLE 12

Effect Of T. harzianum T-39 (I-952) On The Number Of Yeast Cells In Grape Juice Made From Grapes Treated With T-39.

| Treatment in vineyard | Number of yeast cells ($\times 10^4$) Days of Incubation | | | | |
|---|---|---|---|---|---|
| | 1 | 3 | 8 | 11 | 17 |
| Control | 9280 | 12520 | 6000 | 17.8 | 38.2 |
| T. harzianum T-39 | 6960 | 10300 | 1802 | 90.9 | 47.7 |

Differences between treatments at each date were not statistically significant, according to Duncan's Multiple Range Test (P = 0.05).

TABLE 13

Population of T. harzianum T-39 (I-952) On Rose Flowers Treated With Conidia of the Biocontrol Agent

| Days of Incubation | Level of Initial Population | | | |
|---|---|---|---|---|
| | 0 | 1 | 2 | 3 |
| 1 | 0 | $9.0 \times 10^5$ | $2.7 \times 10^7$ | $1.6 \times 10^8$ |
| 3 | 0 | $5.2 \times 10^5$ | $2.3 \times 10^7$ | $4.0 \times 10^8$ |
| 7 | 0 | $2.0 \times 10^5$ | $0.3 \times 10^7$ | $0.8 \times 10^8$ |

TABLE 14

Effect of T. harzianum T-39 (I-952) on Strawberry Gray Mold in Naturally Infested Field[a]

| Treatment | Infected Fruits/10 m row |
|---|---|
| Control | 11.25 |
| T-39 (0.2%) | 6.75 |
| T-39 (0.4%) | 4.50 |
| Folpet (0.25%) | 4.0 |
| Carbendazin + Dithiofencarb (0.1%) | 3.75 |

[a]Spraying was carried out four weeks prior to disease assessment

TABLE 15

Effect of T. harzianum T-39 (I-952) on the Severity of S. sclerotiorum Applied to Carrots After Picking

| Treatment | Disease Index[a,b] |
|---|---|
| Control | 0.714 |
| T-39 (0.2%) | 0.536 |
| T-39 (0.4%) | 0.427 |
| Thiabendazol (0.1%) | 0.821 |

[a]Two weeks after treatment
[b]Key:
0 = No disease
5 = Completely destroyed carrots

TABLE 16

Population Level of T. harzianum T-39 (I-952) on Leaves and Fruit of Cucmber in a Green House

| Sampling Time (Days after Application) | Propagules of T. harzianum | | | |
|---|---|---|---|---|
| | Per Leaf | | Per Fruit | |
| | Untreated | Treated | Untreated | Treated |
| 0 | 54 | 20 | 0 | 0 |
| 28 | 232 | 9000 | 210 | 300 |
| 21 | 2300 | 450000 | 1500 | 350000 |

We claim:

1. A method of controlling the growth of unwanted fungi in flowering plants or fruits comprising applying to the flowering plant or fruit a composition comprising an agricultural carrier and a fungicidally effective amount of a biologically pure, stable culture of an antagonist Trichoderma harzianum I-952 or a mutant derived therefrom which is useful for fungi control.

2. A method in accordance with claim 1, wherein the unwanted fungi Botrytis cinerea.

3. A method in accordance with claim 1 wherein the unwanted fungi is Sclerotinia sclerotiorum.

4. A method in accordance with claim 1, wherein the concentration of the antagonist contained in the culture is at least $10^5$ cells per gram of composition.

5. A method in accordance with claim 1 wherein the antagonist contained in the culture is present in the form of conidia, chlamydospores, or hyphal fragments or mixtures, thereof.

6. A method in accordance with claim 1 wherein the carrier includes a food base for the antagonist contained in the culture.

7. A method in accordance with claim 1 which also comprises a chemical pesticide.

8. A method in accordance with claim 1, wherein the chemical pesticide is a fungicide.

9. A method in accordance with claim 1, wherein the chemical fungicide is chosen from the group consisting of folpet and dicarboximide fungicides.

10. A method in accordance with claim 1, wherein the dicarboximide fungicides are chosen from the group consisting of iprodione and vinclozolin.

* * * * *